United States Patent
Hoganson

(10) Patent No.: US 7,758,654 B2
(45) Date of Patent: Jul. 20, 2010

(54) ANTI-ADHESION DEVICE

(75) Inventor: David M. Hoganson, St. Louis, MO (US)

(73) Assignee: Kensey Nash Corporation, Exton, PA (US)

( * ) Notice: Subject to any disclaimer, the term of this patent is extended or adjusted under 35 U.S.C. 154(b) by 1345 days.

(21) Appl. No.: 10/850,631

(22) Filed: May 20, 2004

(65) Prior Publication Data

US 2005/0261782 A1    Nov. 24, 2005

(51) Int. Cl.
*A61F 2/02* (2006.01)

(52) U.S. Cl. .................. 623/23.74; 623/23.76

(58) Field of Classification Search ............. 623/23.72, 623/23.74, 23.76
See application file for complete search history.

(56) References Cited

U.S. PATENT DOCUMENTS

| | | | |
|---|---|---|---|
| 4,937,254 A | 6/1990 | Sheffield et al. | |
| 5,068,225 A | 11/1991 | Pennell et al. | |
| 5,306,753 A | 4/1994 | Montagna | |
| 5,356,429 A | 10/1994 | Seare | |
| 5,366,472 A * | 11/1994 | Hillstead ................ | 606/194 |
| 5,502,042 A | 3/1996 | Gruskin et al. | |
| 5,502,081 A | 3/1996 | Kuo | |
| 5,505,952 A | 4/1996 | Jiang et al. | |
| 5,508,036 A | 4/1996 | Bakker et al. | |
| 5,580,923 A | 12/1996 | Yeung et al. | |
| 5,593,441 A | 1/1997 | Lichtenstein et al. | |
| 5,631,011 A | 5/1997 | Wadstrom | |
| 5,690,961 A | 11/1997 | Nguyen | |
| 5,711,958 A | 1/1998 | Cohn | |
| 5,791,352 A | 8/1998 | Reich et al. | |
| 5,795,584 A | 8/1998 | Totakura et al. | |
| 5,868,745 A | 2/1999 | Alleyne | |
| 6,013,679 A | 1/2000 | Kuo et al. | |
| 6,030,958 A | 2/2000 | Burns et al. | |
| 6,031,148 A | 2/2000 | Hayes et al. | |
| 6,074,663 A | 6/2000 | Delmotte et al. | |
| 6,096,727 A | 8/2000 | Kuo et al. | |

(Continued)

FOREIGN PATENT DOCUMENTS

CA        2248327        9/1997

(Continued)

OTHER PUBLICATIONS

Becker, et al., "Prevention of postoperative abdominal adhesions by a sodium hyaluronate-based bioresorbable membrane: a prospective, randomized, double-blind multicenter study" *J Am Coll Surg.*, vol. 183, (1996),297-306.

(Continued)

*Primary Examiner*—Thomas J Sweet
(74) *Attorney, Agent, or Firm*—Jeffrey R. Ramberg

(57) ABSTRACT

The construct described herein allows opposing tissues to form adhesions with either side of the construct, as part of the natural healing process. The construct however is multi-layered, wherein the space between the layers provides the protection from unwanted adhesions forming between and bonding separate tissues. In one embodiment, this space between layers of the construct may be developed spontaneously, that is the multiple layers are released by design after a finite time and the opposing tissues are free to move independent of each other, free of adhesions.

59 Claims, 14 Drawing Sheets

U.S. PATENT DOCUMENTS

| | | |
|---|---|---|
| 6,120,539 A | 9/2000 | Eldridge et al. |
| 6,133,325 A | 10/2000 | Schwartz et al. |
| 6,150,581 A | 11/2000 | Jiang et al. |
| 6,235,796 B1 | 5/2001 | Niazi |
| 6,280,745 B1 | 8/2001 | Flore et al. |
| 6,319,264 B1 | 11/2001 | Tormala et al. |
| 6,383,201 B1 | 5/2002 | Dong |
| 6,391,939 B2 | 5/2002 | Tayot et al. |
| 6,410,645 B1 | 6/2002 | Pathak et al. |
| 6,436,425 B1 | 8/2002 | Henry et al. |
| 6,440,427 B1 | 8/2002 | Wadstrom |
| 6,454,767 B2 | 9/2002 | Alleyne |
| 6,486,140 B2 | 11/2002 | Hansson et al. |
| 6,500,777 B1 | 12/2002 | Wiseman et al. |
| 6,518,308 B2 | 2/2003 | Diamond |
| 6,521,223 B1 | 2/2003 | Calias et al. |
| 6,531,146 B2 | 3/2003 | Calhoun et al. |
| 6,534,591 B2 | 3/2003 | Rhee et al. |
| 6,534,693 B2 | 3/2003 | Fischell et al. |
| 6,548,081 B2 | 4/2003 | Sadozai et al. |
| 6,551,610 B2 | 4/2003 | Shalaby et al. |
| 6,566,345 B2 | 5/2003 | Miller et al. |
| 6,579,951 B1 | 6/2003 | Cohn et al. |
| 6,596,304 B1 | 7/2003 | Bayon et al. |
| 6,599,323 B2 | 7/2003 | Melican et al. |
| 6,599,526 B2 | 7/2003 | Dimitrijevich |
| 6,613,325 B1 | 9/2003 | Amery et al. |
| 6,630,167 B2 | 10/2003 | Zhang |
| 6,652,595 B1 | 11/2003 | Nicolo |
| 6,656,488 B2 | 12/2003 | Yi et al. |
| 6,773,458 B1 * | 8/2004 | Brauker et al. ............ 623/11.11 |
| 6,977,231 B1 * | 12/2005 | Matsuda ..................... 442/370 |
| 2003/0212462 A1 | 11/2003 | Gryska et al. |

FOREIGN PATENT DOCUMENTS

| | | |
|---|---|---|
| EP | 0334046 | 9/1989 |
| EP | 1384450 | 1/2004 |
| WO | WO-02/02015 | 1/2002 |

OTHER PUBLICATIONS

Dizerega, Gere S., "Contemporary Adhesion Prevention, Fertility and Sterility", 61(2), (Feb. 1994),219-235.

Harris, Elizabeth S., et al., "Analysis of the kinetic fo perioneal adhesion formation in the rat and evaluation of potential antiadhesive agents", *Surgery*, vol. 177, No. 6, (Jun. 1995),663-669.

Hellebrekers, B. W., et al., "Effects of five different barrier materials on postsurgical adhesion formation in the rat", *Hum Reprod.* 15(6), (Jun. 2000),1358-1363.

Hershlag, Avner, et al., "Adhesiolysys", *Clin Obstet Gynecol*, 34(2), (Jun. 1991),395-402.

Monk, Bradley J., et al., "Adhesions after extensive gynecologic surgery: clinical significance, etiology, and prevention", *Am J Obstet Gynecol.*, 170(5 part 1). (1994),1393-1403.

Okuyama, M.D., Naoki, et al., "Prevention of Retrosternal Adhesion Formation in a Rabbit Model Using Bioresrobable Films of Polyethylene Glycol and Polylactic Acid", *Journal of Surgical Research*, V. 78,(1998),118-122.

Oncel, M.D., Mustafa, et al., "Comparison of a Novel Liquid (Adcon-P.R) and a Sodium Hyaluronate and Carboxymethylcellulose Membrane (Seprafilm.TM) in Postsurgical Adhesion Formation in a Murine Model", *Dis Colon Rectum*, V. 46, No. 2,(Feb. 2003),187-191.

* cited by examiner

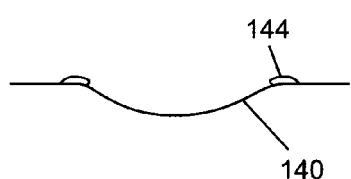
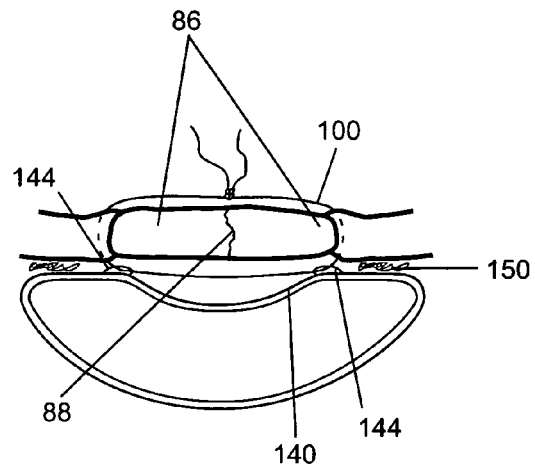
Fig. 13     Fig. 14
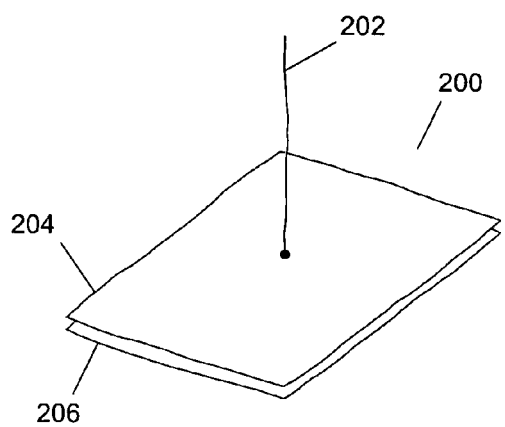
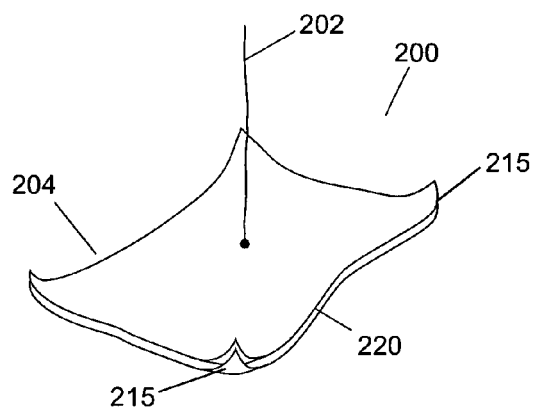
Fig. 15     Fig. 16

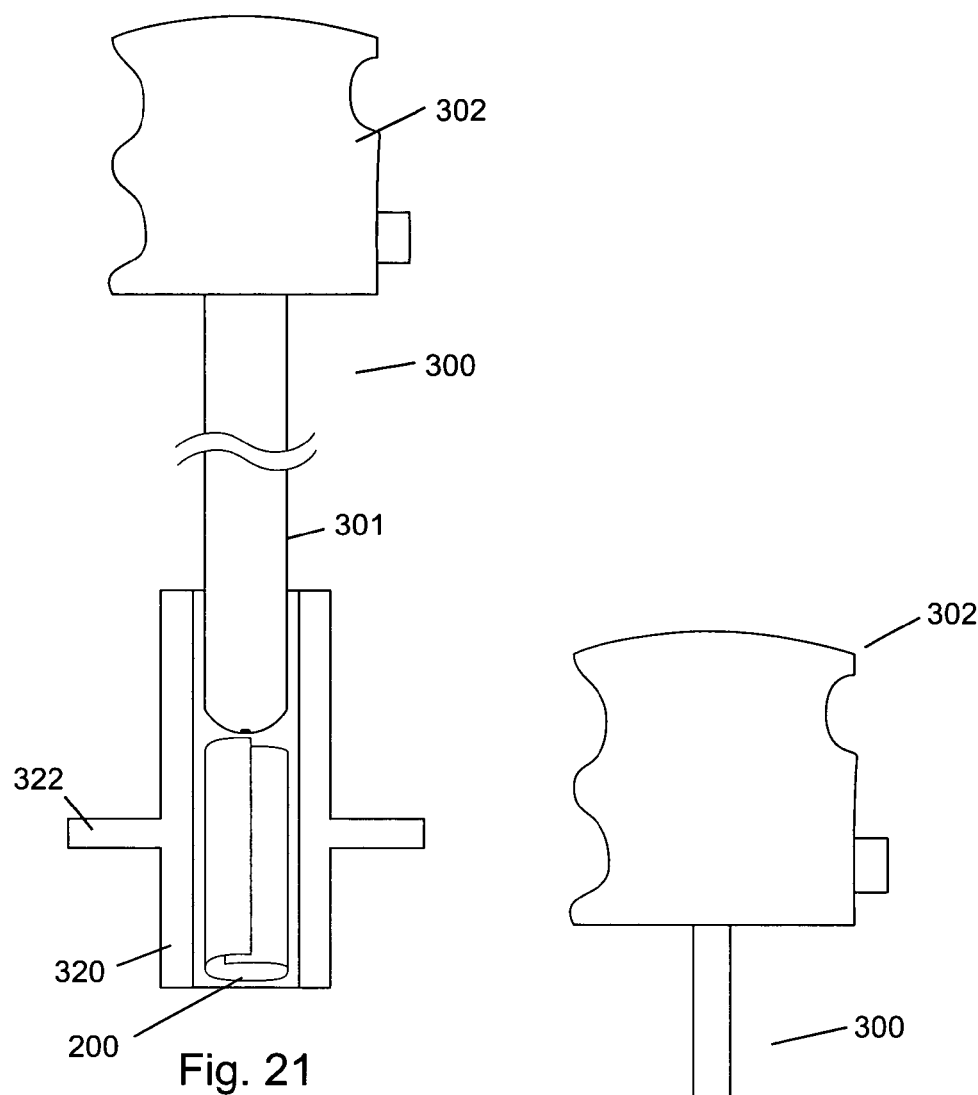
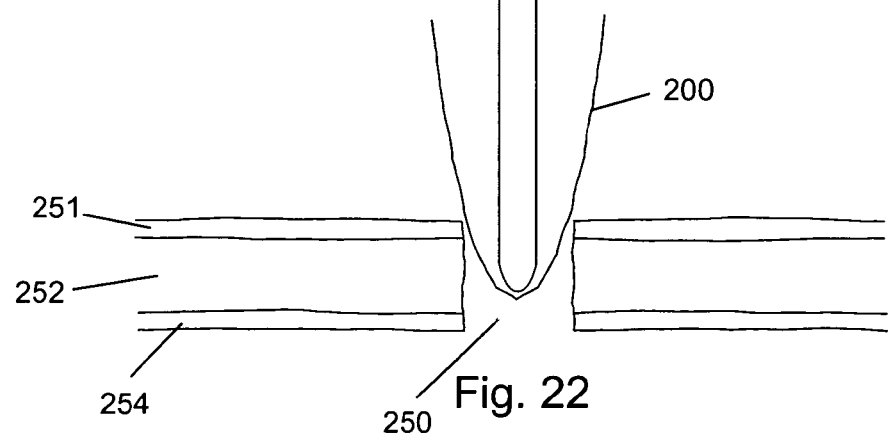

ANTI-ADHESION DEVICE

BACKGROUND OF THE INVENTION

The invention generally relates to implantable devices, specifically relating to devices for the prevention of unwanted scar tissue. The invention more particularly concerns a multi-layered device which serves to prevent unwanted adhesion formation following a surgical procedure.

Adhesions following surgery are a common result of the body's natural healing process. Unfortunately, nearly all surgeries have the risk of unwanted adhesions. Some adhesions cause or can lead to significant morbidity or mortality for the patient. For example, adhesions which follow abdominal or pelvic surgery may lead to bowel obstruction for the patient within months or even up to years subsequent to the original surgery. Many adhesions increase the risk and difficulty of second operations. Repeat cesarean sections are much more difficult and can risk injuring the uterus or bladder if significant post-operative adhesions are present. Adhesions following cardiac surgery also greatly increase the risk of a second operation. Approximately fifteen percent of cardiac surgery are "redo" or repeated surgeries. In these "redo" cases, the heart, bypass grafts or great vessels can be injured during the repeat sternotomy due to adhesions holding these structures against or near the sternum. In these cases, significant pre-sternotomy preparation must be performed, such as preparation of the groin for possible cannulation and peripheral cardiopulmonary bypass in the event that the heart or a great vessel is injured during the sternotomy. Additionally the presence of adhesions adds a tremendous amount of time and difficulty to any surgery. Overall, adhesions increase the risk and cost of any repeat surgery.

It is believed that the inflammatory process which results in adhesions occurs in the first few days following an operation or procedure. The single concept to date in anti-adhesion barrier technology has been a biomaterial which separates tissues and prevents the adhesion of tissues to the biomaterial or to one anther. Currently available single layered anti-adhesion barriers have only had some success at preventing these post-operative adhesions. Adhesions do occur in the area where the resorbable barriers were placed. In the design of these single layered barriers, the thought is that they will physically separate the tissues for longer than the first few post-operative days and then be resorbed. Additionally these barriers are composed of material believed to be anti-adhesive in nature. These single layered or functionally single layered (multiple layers which do not separate or have designated middle layers to provide physical separation between outer layers) may fail to completely prevent adhesions because the opposing tissue actually forms one or more adhesions to the barrier material. When the barrier material is resorbed, if adhesions have formed on opposite sides of the material, those tissues will then likely remain bonded to each other as the resorbable material between them degrades. In summary, single layered or functionally single layered barriers are inadequate to prevent adhesions possibly due to the incomplete anti-adhesive quality of their materials and the limitation of their design in that their success is based on the anti-adhesive quality of their materials. There have been a number of materials and forms of materials with this approach.

U.S. Pat. No. 6,030,958 (Burns et al.) describes a film constructed from a polyanionic polysaccharide which is placed between tissues and remains there long enough to prevent the tissues from healing together. The film then disperses and is completely resorbed into the body.

U.S. Pat. No. 6,548,081 (Sadozai et al.) describes an anti-adhesion composite constructed from hyaluronic acid and a carboiimide. This composite can be a sustained release source of hyaluronic acid to prevent adjacent tissue adhesion.

U.S. Pat. No. 6,391,939 (Wells et al.) describes a construct for the prevention of adhesions derived from collagen. In one embodiment, the collagen is combined with polyethylene glycol to form a construct which will be resorbed in less than one week.

U.S. Pat. No. 6,500,777 (Wiseman et al.) describes a construct for the prevention of adhesions which is a continuous film of oxidized cellulose. The construct is formed in a multi-layer sandwich of cellulose film on the outside and a middle layer such as rayon or a fabric to provide mechanical strength. The cellulose film is non-porous to prevent adherence of cells and molecules to the cellulose film. The middle layer of the construct adds enough strength so it can be sutured. The cellulose film can also be used without the middle layer.

U.S. Pat. No. 5,795,584 (Totakura et al.) describes a surgical adhesion barrier constructed of at least one bioabsorbable polymer. This barrier may be formed from one or more layers of polymers. The polymers may be a combination of resorbable and non-resorbable polymers. The barrier may also contain a medicinal agent between the layers.

U.S. Pat. No. 6,074,663 (Delmotte et al.) describes a bio-mechanical barrier for the prevention of post-operative adhesions formed from cross-linked fibrin. The fibrin film may be multi-layered and may have very small pores to prevent the formation of adhesions to the film.

U.S. Pat. No. 5,356,429 (Seare) describes an elastomeric barrier material that may serve to prevent the re-adherence together of body pocket walls around an implantable prosthesis. Seare describes a dual layer material, with the two outwardly facing opposite sides being textured to encourage cell growth, and the two inside facing surfaces being smooth and non-textured to readily slide with respect to one another. In this embodiment, the two textured sides would adhere to the corresponding tissue surfaces, while the two smooth sides would remain slidable relative to each other, thereby preventing the re-adherence of tissue surfaces.

In summary, the current anti-adhesion technologies strive for a barrier material which will physically separate the tissues without migration, prevent the adhesion of tissue to the barrier, and be resorbed within a few weeks after the adjacent tissues have reduced their propensity to adhere to one another. The delivery of medicinal agents by these barrier materials has also been proposed.

Unfortunately, these anti-adhesion technologies only prevent formation of the adhesions in fifty percent or less of the surgical cases. What is needed is a technology which will overcome the limitations of current anti-adhesion devices allowing the body to form post-operative adhesions in a defined manner and positioning the anti-adhesion construct so the desired surgical and anatomical planes remained preserved.

SUMMARY OF THE INVENTION

In accordance with one embodiment of the invention, the construct described herein allows opposing tissues to form adhesions with either side of the construct, as part of the natural healing process. The construct however is multi-layered, wherein the space between the layers provides the protection from unwanted adhesions forming between and bonding separate tissues. In one embodiment, this space between layers of the construct may be developed spontaneously, that is the multiple layers are released by design after a finite time and the opposing tissues are free to move independent of each other, free of adhesions. Alternatively the space between the layers of the construct may be developed surgically during a second surgical procedure.

In accordance with one preferred embodiment of this invention, the device is placed posterior to the sternum following a sternotomy to prevent adherence of the contents of the thorax to the posterior wall of the sternum. The device allows for a subsequent sternotomy to be performed without injuring tissues posterior to the sternum.

In another embodiment, the device may be placed between the uterus and the posterior layer of the anterior abdominal wall following a cesarean section to allow for safe entry into the abdomen in the event that a subsequent cesarean section is necessary.

In one embodiment, the device may be a multi-layered construct. These layers may be sealed to one another along the edges to create a potential space between the two layers (e.g., a sleeve). The construct may have projections from one surface to facilitate approximation of the construct to desired tissue (i.e. the posterior portion of the sternum). In the event that the tissue overlying the device (i.e. sternum) is reopened, the anterior layers of the construct may be cut but the posterior layer may be preserved thereby protecting the tissues beneath the posterior layer from inadvertent injury. The layer (s) of the construct which are not initially cut may have certain properties which protect the tissue behind or below them by preventing inadvertent division of those layers.

In accordance with another aspect of this invention, the construct may have mechanical properties or may incorporate agents which promote adhesion of the one or more layers of the construct to a tissue and/or may prevent adhesion of one or more layers to a tissue. Additionally, the construct may incorporate additive components, such as therapeutic agents which are released into the tissues adjacent to and in the general area of the construct which may have beneficial effects on those tissues and/or the living being as a whole. These various embodiments may be adaptable to various surgical applications, and the examples herein are not meant to be limiting but rather illustrative.

DESCRIPTION OF THE DRAWINGS

Other aspects and many of the attendant advantages of this invention will readily be appreciated as the same becomes better understood by reference to the following detailed description when considered in connection with the accompanying drawings wherein:

FIG. 13 is an enlarged sectional view of another embodiment of the device where the construct may have a preformed shape;

FIG. 14 is an enlarged sectional view of the construct shown in FIG. 13 where the construct is adjacent to the posterior sternum;

FIG. 15 is an isometric view of an embodiment of the device;

FIG. 16 is an isometric view of an embodiment of the device where the construct has a non-planar shape;

FIG. 21 is a cross-sectional view of a delivery system for delivering the construct into a body cavity;

FIG. 22 is a cross-sectional view of another embodiment of a delivery system for delivering the construct into a body cavity;

DETAILED DESCRIPTION OF PREFERRED EMBODIMENTS

Before the anti-adhesion constructs are described, it is to be understood that this invention is not intended to be limited to the particular constructs and methods described in the preferred embodiments, as one skilled in the art can extend the concepts involved using variations which are obvious after reading the present disclosure.

It must be noted that, as used in this specification and the appended claims, the singular forms "a", "an", and "the" include plural referents, unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, preferred compositions, films, methods and materials are described below.

Figure 1:
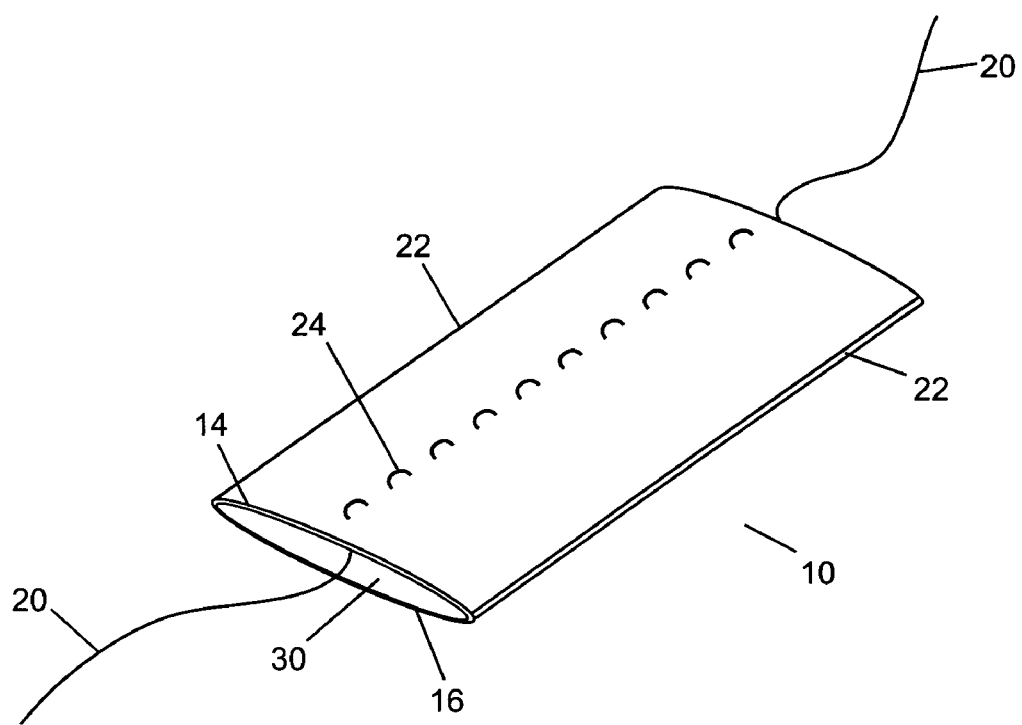
FIG. 1 is an illustration of a multi-layered embodiment of the construct.

Referring now in greater detail to the various figures of the drawings, wherein like reference characters refer to like parts, there is shown in FIG. 1 a construct 10 for preventing adhesion between adjacent tissues. This embodiment of the construct provides temporary or permanent mechanical separation between tissues. The construct 10 is depicted as a multiple layered device having an anterior layer 14 and a posterior layer 16. The layers 14 and 16 may be affixed or attached together at a joint 22, depicted in this embodiment as opposing edges. It is recognized that the layers may be joined in other fashions or manners suitable for a particular purpose. In an embodiment, the perimeter edges of the construct may be joined together, forming a joint extending around all the edges of the device, resulting in a sealed space or pocket defined within. The construct 10 may incorporate multiple layers, including multiple anterior and/or multiple posterior layers. Additionally, there may be middle layers in the construct. The layers may be joined by joint 22 at a single point, at multiple points, or in a substantial manner across the two opposing surfaces of the layers. Some portion of the layers, such as the edges of the layers as depicted in FIG. 1, may be affixed to each other, either permanently or temporarily, by some fashion known in the art (e.g., adhesives, static, mechanical interaction, fasteners, welding, etc.) to form joint 22.

In an embodiment, the attachment between the layers may be formed without any adhesive material. One such method of attaching the layers is physical compression. This may be done with or without the application of heat. Such a method of weakly adhering the layers may allow for them to appear as a single sheet when handling and on placement but after placement or implantation in the body, the layers may lose their physical connection but may remain approximated to each other. Joining the layers at the edges may create a real or potential space 30 between the layers. If the layers are joined on all sides, the space 30 becomes completely enclosed (e.g., a sleeve, or a pocket) and isolated from the outside of the construct.

The multi-layer construct may have means of securing the device and to assist in approximating the construct to the adjacent tissue. As shown in FIG. 1, a series of loops 24 may be arranged along the anterior surface of the construct. These loops 24 may be used with suture or sternal wires to approximate the construct to the posterior wall of the sternum or other tissue. The loops may be constructed of the same material that is used for the layer(s) of the construct or may be different material. They may be radiopaque. They may be spaced at uniform or various distances (not shown) down the midline of the construct or may be placed at any point on the outside of the construct. Additional embodiments may include tabs of material which may be penetrated with suture or wire. Such tabs may be present on the surface of the outer layer of the construct or may extend off the surface of the layer. Alternative methods of securing the construct to the posterior portion of the sternum or any other tissue may be employed, including but not limited to, suturing the construct, adhesives, magnetic forces, or staples.

In the event that the tissues in which the construct is placed need to be explored again during an operation it would be advantageous to easily locate the construct (e.g., through the detection of a locating means). The locating means may, in one embodiment be a locating limb 20 of the construct 10, which may be placed in an area which would be accessed during reoperation so the location of construct may be identified. There may be one or more limbs 20 of the graft. The location of the limbs may be on either side of the construct or on the edges. Alternatively the limb(s) 20 may be connected to one another or may be a single limb with one or more attachment points on the construct. As such, the loops 24 could be considered a form of a location limb.

Figure 2:
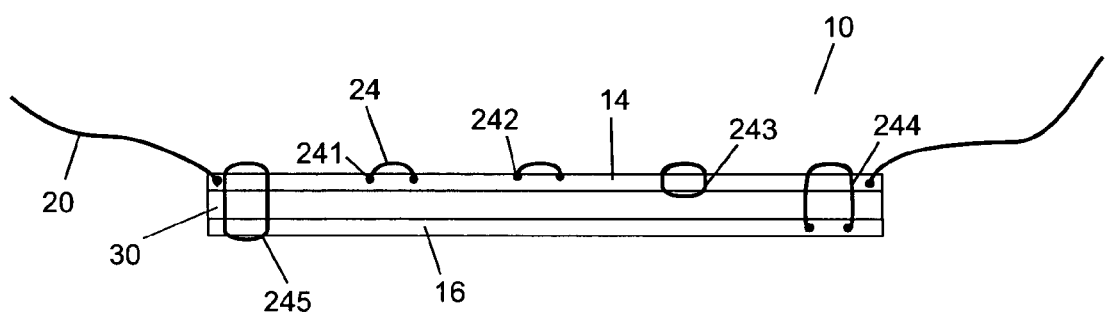
FIG. 2 is an enlarged sectional view of the construct shown in FIG. 1.

FIG. 2 is a side view of the construct 10 where anterior 14 and posterior 16 layers are shown. Additionally, multiple loops 24 are shown as are locating limbs 20. This figure demonstrates the potential or real space 30 that is present between the layers. After the construct 10 is implanted, this space 30 may be considered potential as the anterior 14 and posterior 16 layers of the construct may contact each other, and may be separated later to form the space. The loops 24 may be anchored to the construct to prevent their removal. They may be attached to the construct at different points as is shown in FIG. 2. Shown at connection 241, the loop 24 is attached to the surface of the anterior layer 14. The loop 24 may also be attached to the middle of the anterior layer 14 as seen at connection 242, and extends through the anterior layer as shown at connection 243, attaches to the posterior layer as seen in connection 244, or extends entirely through both the anterior and the posterior layers as seen in connection 245. The mechanical attachment of the loop may be accomplished by a variety of methods known in the art, e.g., it may be incorporated into the construct while it is made or as a post-processing step after the construct layers are formed. The loop 24 also may be molded into a particular portion of the construct. Alternatively, it may be sutured, stapled, glued or attached by heat processing.

The material used for the construct may be constructed of various materials. In one embodiment, the construct may be manufactured from at least one non-resorbable polymer known in the art (e.g., polyurethane, polystyrene, polyethylene, polycarbonate, polyester, nylon, polytetrafluoroethylene, polyethylene terephthalate, aramid, etc.). Using a non-resorbable material, such as polymers or metals, would ensure that the construct would be present for several years, or even decades later, in the event that the sternum or other protected tissue would need to be reoperated upon.

There may be applications of the construct where a resorbable material is preferred. Alternatively, a combination of resorbable and non-resorbable materials may be used. A representative, but not exhaustive, list of resorbable materials is shown in Table 1.

TABLE 1

Examples of Biodegradable Polymers for Construction of the Device

Aliphatic polyesters
Bioglass
Carboxymethylcellulose
Cellulose
Chitin
Citrate
Collagen
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/ε-caprolactone copolymers
Lactide/σ-valerolactone copolymers
L-lactide/dl-lactide copolymers
Methyl methacrylate-N-vinyl pyrrolidone copolymers
Modified proteins
Nylon-2
PHBA/γ-hydroxyvalerate copolymers (PHBA/HVA)
PLA/polyethylene oxide copolymers
PLA-polyethylene oxide (PELA)

TABLE 1-continued

Examples of Biodegradable Polymers for Construction of the Device

Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyethylene Glycol
Polyethylene Oxide
Polyglycan Esters
Poly(Glycerol Sebacate)
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β-hydroxypropionate (PHPA)
Poly-β-hydroxybutyrate (PBA)
Poly-σ-valerolactone
Poly-β-alkanoic acids
Poly-β-malic acid (PMLA)
Poly-ε-caprolactone (PCL)
Pseudo-Poly(Amino Acids)
Starch
Trimethylene carbonate (TMC)
Tyrosine based polymers In addition to the type of material, the form of the material may be important in achieving optimum protection of the tissues. The material may be at least partially formed as a porous or foamed construct. In alternative constructs, the device may be at least partially formed as a gel, a solid sheet, a composite, a laminate or even a bag.

Figure 3:
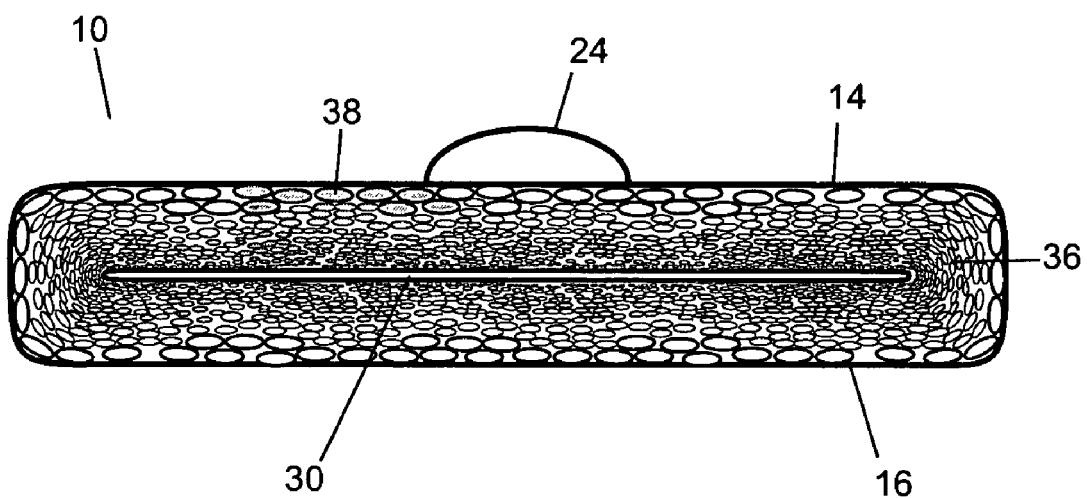
FIG. 3 is an enlarged sectional view of the construct shown in FIG. 1.

In one embodiment of the construct, at least a portion of the material may be porous. FIG. 3 is a depiction of a construct 10 where the layers 14 and 16 of the construct are made with an open porous structure 36. The porous structure 36 may extend thorough the entire thickness of a layer or only through a portion of the thickness of a layer. For example, the pores may extend from the outer surface of the construct and the inner surface of the layers of the construct may be impermeable. The pores may be of a uniform size or shape, alternatively the pores may vary throughout the construct. In one embodiment, the pores form a gradient, varying either in size or number from one surface to the other. For example the pores may be larger near the outer surface of the layers and smaller near the inner surface of the layers.

In one embodiment, it may be advantageous to incorporate additive components 38 within at least a portion of the construct 10. The additives 38 may add or modify a quality of the device, or serve to improve the function of the device. The additive components may be contained entirely within the pores 36, entrained within the polymer material of the construct, or alternatively the additive components may be located in both the polymer material and the pores of the construct. The additive component 38, in combination with the material making up the layers of the construct, may combine to have many functions.

The additive component 38 may, for example, be a biologically active agent, or a carrier material for a biologically active agent which may, among other uses, serve as a drug therapy for localized or systemic delivery, serve to promote adhesion of the construct to a tissue, serve to prevent adhesion of the construct to a tissue, serve to attract or repel cells, or otherwise promote or inhibit cell growth. In the case of a resorbable device, the biologically active agent may be delivered as the device is bioeroded, exposing previously shielded pores, materials and/or drugs, alternatively, the biologically active agent and/or material could be delivered in a finite period of time, leaving the device to be bioeroded more slowly. It is also recognized that more than one additive component may be incorporated into the device. For example, in a case where more than one biologically active agent is delivered, the first may be a drug that is very quickly delivered, and a second may be a cell growth inhibitor that is persistent within the device and is delivered more slowly, such that staggered or different delivery periods are possible. In a non-resorbable embodiment, an amount of additive component may be added to the device in order to be delivered to the body, such that the additive is delivered for a finite period of time or dosage.

Additionally, the additive component 38 may also be a structural agent, such as plasticizers, reinforcing sheets, ceramics, fibrous materials, or particulate materials that alter the mechanical properties of the device or one of its layers. Among the ways that the mechanical properties of the layers may be altered is exhibited through an increase or decrease in elasticity, strength or toughness, enhanced resistance to penetration or cutting, enhanced resorption time of the construct.

The porous nature of the material or other material properties as described above may promote local adhesions that are beneficial. For example, if the material is used in an area of the body which has recently been repaired (i.e bowel anastomosis or other suture or staple line) the promotion of local adhesions between one layer of the material and the adjacent portion of the body may improve or otherwise allow natural healing to occur. Furthermore, the presence of the construct may prevent the appearance of non-desired adhesion of such repaired tissue to other tissue, while allowing repaired tissue to adequately heal.

The porous nature of the material or other material properties or additives as described above may be beneficial in promoting approximation or adherence of the construct to tissues. The material may also change shape (i.e. shrink, expand, or flex) to conform to and adhere to tissues. The application of heat or raising the temperature of the material from room temperature to or above body temperature may play a role in this process. Additionally, heat, electricity or other forces or chemicals may be used to change the material prior to or after implantation to improve its position within the body and its adherence to tissue.

Figure 4:
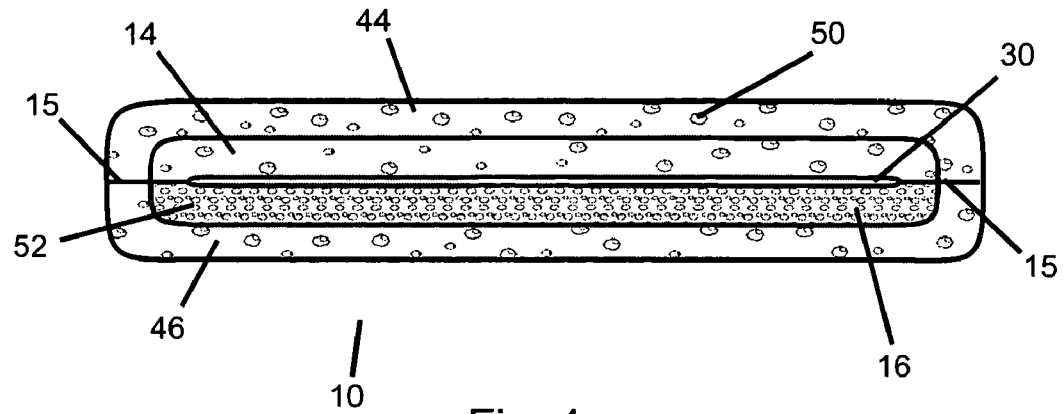
FIG. 4 is an enlarged longitudinal sectional view of the construct shown in FIG. 1.

FIG. 4 shows an alternative method of creating discontiguous properties through or around a construct, such as may be achieved by incorporating at least one additive components 50 and 52 within the construct. In a preferred embodiment, sections 14 and 16 may be dissimilar materials or a material with dissimilar properties, wherein said sections are connected, by methods known in the art, at a seam 15. The construct 10 in FIG. 4 is a multi-layered construct with anterior layers 44 and 14 and posterior layers 46 and 16. Incorporated into the layers of the depicted embodiment is a material 50 associated with outer layers of 44 and 46 and inner layer 14, while material 52 is associated with inner layer 16. It is recognized there may be multiple layers, and layers making up the anterior and posterior surfaces or one or more middle layers, may not be the same in number, material, thickness, additive component, or other properties. Similarly, the materials 50 and 52 within the layers may be different, may be incorporated into some layers and not others, or with any combination of layers and additional materials. Alternatively, the space 30 could be filled with an additive component material (not shown) (e.g., a therapeutic or pharmaceutical agent, a biologically active agent, a structural agent, a nanoparticle, a radiopaque or nuclear agent, etc.). A non-exhaustive list of examples of therapeutic or biologically active agents is shown in Table 2.

The therapeutic agent or other material may be added with other additive components, creating a construct having more than one incorporated material. In the configuration of a porous construct as shown in FIG. 3, an additive component 38 may be a therapeutic agent capable of being delivered with a carrier material inside the construct, herein shown as contained within a portion of the pores 36 of the construct 10. The materials added with the therapeutic agent may alter the properties or release of the therapeutic agent.

TABLE 2

Examples of Biological, Pharmaceutical, and other Therapies Deliverable via the Present Invention Adenovirus with or without genetic material
Alcohol
Amino Acids
    L-Arginine
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents
    Forskolin
    GP IIb-IIIa inhibitors
        eptifibatide
Anti-proliferation agents
    Rho Kinase Inhibitors
        (+)-trans-4-(1-aminoethyl)-1-(4-pyridylcarbamoyl)
        cyclohexane
Anti-rejection agents
    Rapamycin
Anti-restenosis agents
    Adenosine $A_{2A}$ receptor agonists
Antisense
Antispasm agents
    Lidocaine
    Nitroglycerin
    Nicarpidine
Anti-thrombogenic agents
    Argatroban
    Fondaparinux
    Hirudin
    GP IIb/IIIa inhibitors
Anti-viral drugs
Arteriogenesis agents
    acidic fibroblast growth factor (aFGF)
    angiogenin TABLE 2-continued Examples of Biological, Pharmaceutical, and other Therapies Deliverable via the Present Invention angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
Chemotherapeutic agents
    Ceramide
    Taxol
    Cisplatin
Cholesterol reducers
Chondroitin
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Bone morphogenic proteins (BMPs)
    Core binding factor A
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Transforming growth factors alpha (TGF-alpha)
    Transforming growth factors beta (TGF-beta)
    Vascular Endothelial Growth Factor (VEGF)
    Vascular permeability factor (UPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
inflammatory mediator
Insulin

TABLE 2-continued

Examples of Biological, Pharmaceutical, and other Therapies Deliverable via the Present Invention Interleukins
    Interlukin-8 (IL-8)
    Interlukins
Lipid lowering agents
Lipo-proteins
Low-molecular weight heparin
Lymphocites
Lysine
MAC-1
Methylation inhibitors
Morphogens
Nitric oxide (NO)
Nucleotides
Peptides
Polyphenol
PR39
Proteins
Prostaglandins
Proteoglycans
    Perlecan
Radioactive materials
    Iodine - 125
    Iodine - 131
    Iridium - 192
    Palladium 103
Radio-pharmaceuticals
Secondary Messengers
    Ceramide
Somatomedins
Statins
Stem Cells
Steroids
Thrombin
Thrombin inhibitor
Thrombolytics
Ticlid
Tyrosine kinase Inhibitors
    ST638
    AG-17
Vasodilators
    Histamine
    Forskolin
    Nitroglycerin
Vitamins
    E
    C
Yeast
Ziyphi fructus The inclusion of groups and subgroups in Table 2 is exemplary and for convenience only. The grouping does not indicate a preferred use or limitation on use of any drug therein. That is, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include all forms.

Figure 5:
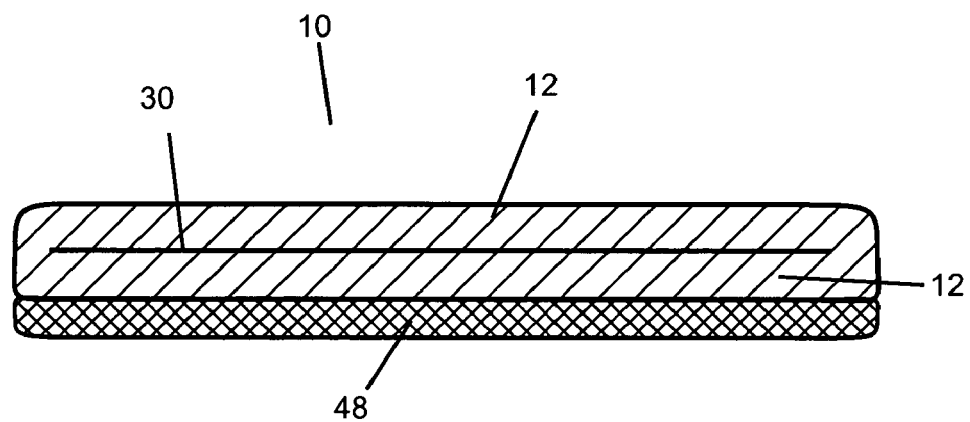
FIG. 5 is an enlarged sectional view of another embodiment of the construct with multiple layers and additional material incorporated in the construct.

In some applications of the construct it may be advantageous for portions of the construct to be stronger or reinforced. FIG. 5 shows a construct 10 where a portion of the construct is an encircling structure 12 which may form a space 30 within it. In a preferred embodiment, said encircling layer is collapsed (as shown) thereby effectively creating a discontinuity from the anterior to posterior side. This discontinuity may serve various functions (e.g., inhibiting cell crossing) while collapsed and may serve alternate functions when opened to form a void space (as will be discussed).

A reinforcing layer 48 may be attached to the construct outside the encircling layer 12. The reinforcing layer 48 could also be positioned within the encircling layer 12, either within the space 30, or embedded within the layer 12. The reinforcing materials (e.g., aramid, metal, carbon fiber, tetrafluoroethylene, polyester, nylon, etc.) could be incorporated into the construct 10, as separate particles, fibers, weaves, meshes, sheets, films, coatings, etc. In some embodiments, the reinforcing layer may incorporate a plurality of components or layers that collectively form the reinforcing layer 48. The reinforcing portion of the construct may serve various functions, such as structural support, and/or prevent incidental penetration of a portion of the construct. In one embodiment, if the construct is placed posterior to the sternum following a surgery involving a median sternotomy, the reinforced layer may protect structures posterior to the construct from inadvertent injury in the case that the sternum needs to be reopened in a subsequent operation.

In another embodiment, the device may feature an intervening sheet or layer of material separating two opposing layers of the device (e.g., an anterior layer and a posterior layer), so that the intervening sheet or layer of material may serve to prevent or reduce the occurrence of adhesions between the two opposing layers. Similarly, the intervening sheet or layer of material may serve to reduce friction between the two opposing layers. This intervening sheet or layer of material may be made from one or more resorbable or non-resorbable polymers, either the same as, or different from the polymer making up the rest of the construct.

Figure 6:
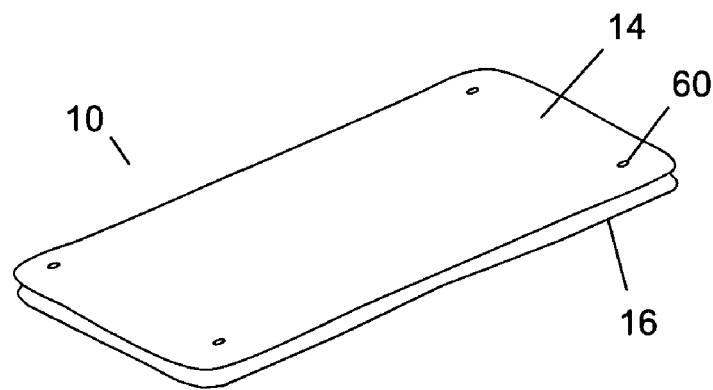
FIG. 6 is a perspective view of another embodiment of the construct with multiple layers.

The layers of the construct may be attached to each other by some means at one or more points. FIG. 6 shows one embodiment where the construct 10 has an anterior layer 14 and posterior layer 16 which are attached at one or more points 60. The attachment point(s) 60 may be a temporary or permanent attachment created through some attachment means. The layers 14 and 16 may be releasably attached, that is they may be physically attached or merely spatially approximated on application or insertion, wherein after some time they are no longer physically attached or may be no longer spatially approximated.

Figure 7A:
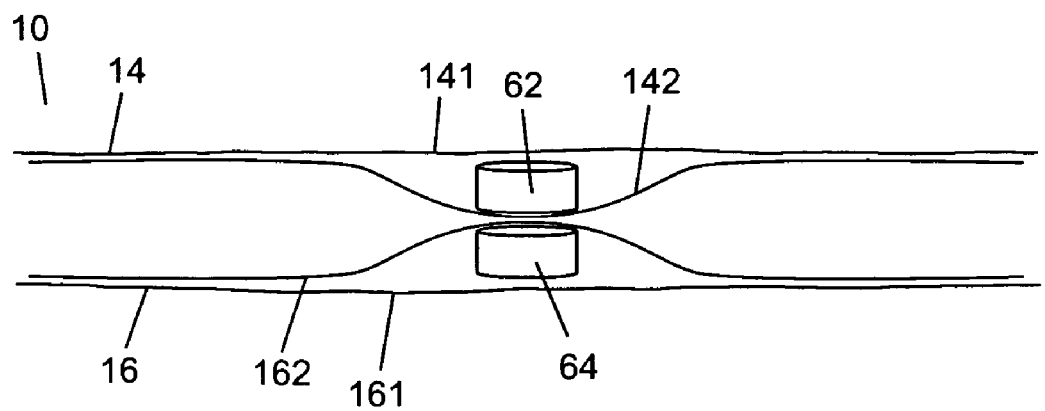
FIGS. 7A, B, and C are illustrations of a multi-layered embodiment of the construct, having attachments between the layers of the construct in the form of magnetic materials, sutures, and multiple attachments, respectively.

FIG. 7a shows one embodiment of an attachment means between two layers of a construct. The construct 10 has anterior layer 14 and posterior layer 16. Each of the anterior 14 and posterior 16 layers have a portion of the layers which separate to form separate layers 141 and 142 for the anterior layer 14 and 161 and 162 for the posterior layer 16. Within the separated layers 141 and 142 there may be a magnetic material 62. This magnetic material 62 may be opposing a second magnetic material 64 within the posterior layers 161 and 162. The two opposing magnetic materials may form a temporary or permanent attachment between the layers 14 and 16. The magnet may be incorporated into one of the layers and attracted to another material such as sternal wires. The magnet may be incorporated with or attached to the layers with methods other than in a pocket between the layers. Another method of attaching a magnetic material to a construct is to incorporate a metal or other magnetizable material into the construct. Alternative embodiments of a means to facilitate attachment include suturing, gluing or heat melting.

Figure 7B:
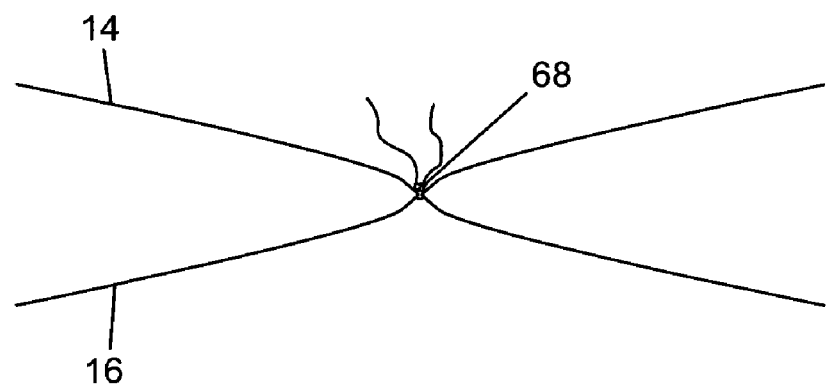

FIG. 7B depicts an alternative attachment means between opposing layers of the construct. The anterior 14 and posterior 16 layers of the construct may be attached with a tightening attachment mechanism 68. This tightening attachment mechanism 68 may be a suture or other flexible elongated material. Alternatively it may be a staple, clip or other similar device. Still another embodiment of a means facilitating the attachment 68 is a multi-part attachment which locks together, such as two components that form a friction fit to be snapped or locked in place.

The means for attachment 68 may be applied during manufacturing of the device or may be applied in the operating room during the surgery. The attachment 68 may be made in such a way to release after a period of time so the layers 14 and 16 would be completely separate. This may be done in a number of ways with the attachments described above. Using a magnetic attachment, a temporary magnet could be used which would over time, lose its magnetic field and release the attachment between the layers. Another attachment method, such as the one shown in FIG. 7B, may incorporate a material that attaches temporarily, such as a resorbable polymer, which degrades over time and releases the opposing layers. The choice of material and design of the releasable attachment could determine the time or the conditions in which the attachment would release. Other materials and manners to effectuate attachment means may incorporate a salt, a carbohydrate, gelatin, hydrogel, static bond created through static electricity, or may include, but not be limited to, any of the materials listed in tables 1, or any combination of the above.

A multi-layered construct in which the layers releasably separate after a given time may be very useful in preventing adhesions in a number of surgical applications. Such a construct may be very useful in a cesarean section where the anterior wall of the uterus may adhere to the peritoneum or posterior fascial wall. Additionally, it may be used in, but not limited to, abdominal, pelvic, neuro, plastic, urologic, orthopedic, or cardiothoracic surgery to prevent the formation of unwanted adhesion of tissue.

Figure 7C:
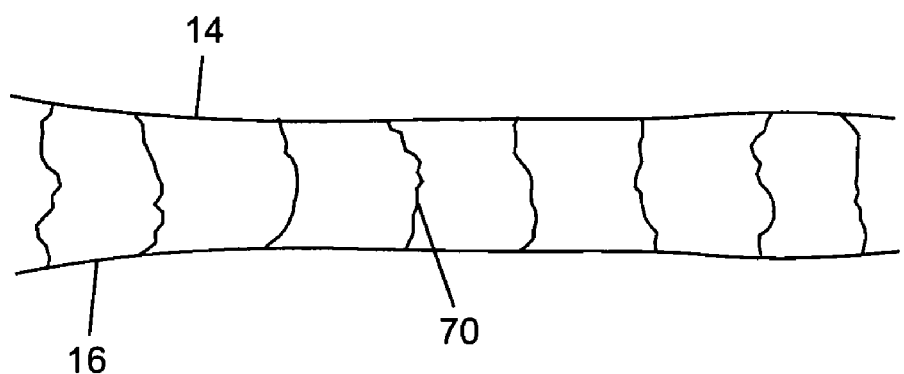

FIG. 7C shows another attachment embodiment wherein the layers 14 and 16 are connected by at least one attachment 70. As depicted, the at least one attachment may preferably be a plurality of closely spaced attachments 70. The attachments 70 may hold the layers adjacent to each other or at a distance apart. These attachments 70 may also be temporary in nature. It may be advantageous to have many lower strength attachments closely spaced over the construct, as opposed to a few more robust attachments in the construct (such as can be seen in FIG. 6). Such attachments may be composed of those as described above. Other attachment materials may include polyethylene glycol or hylauronic acid.

The present invention overcomes the limitations of current anti-adhesive barriers by improved design. Rather than trying to prevent adhesion of tissues to a barrier material, in one embodiment this design allows adhesion of tissues to the opposing layers of the barrier but prevents adhesion between opposing layers of the barrier. With this design, in the first few days after the operation when the tissues are forming adhesions, the outside surfaces of the barrier may adhere to the adjacent tissues. During or after the initial period of inflammation and adhesion formation, there may be a release of the physical connection between the opposing outer layers by incorporation of a temporary attachment as described above (e.g., a carbohydrate or polyethylene glycol bond is dissolved). The plane between these layers defines the new plane between the tissues. The opposing tissues may each be adhered to a layer of the original barrier and they can move relative to each other as there is no attachment between the respective layers of the barrier. The respective separated layers may then be resorbed over time leaving no adhesive connection between the adjacent tissues. It may be important for the material and thickness of the layers of the barrier designed such that the layers are not resorbed in the time that the tissues are forming adhesions.

One preferred embodiment of such a design may be a two layered device like that shown in FIG. 6 where layers 14 and 16 are each composed of a resorbable polymer which has a relatively short resorption time (i.e. 50/50 PLA/PGA copolymer) and is manufactured with a plasticizer (e.g., polyethylene glycol or citrate) to improve flexibility. The layers 14 and 16 may be porous on the outer surfaces but non-porous on the surfaces which oppose each other. This would allow or encourage adherence of tissue to the outer layers but prevent tissue from encroaching on the space between the layers until the polymers layers are resorbed. The bond at attachment point 60 between the layers 14 and 16 may be formed by drying a carbohydrate, polyethylene glycol, or hylauronic acid solution. This would form a relatively weak connection between the layers but one that would make the barrier feel like a single sheet to the surgeon. After hours or days, the bond between the layers would be resorbed or dissolved and the layers would be physically isolated. Subsequent to the resorption or dissolving of the bond at attachment points 60, there is no physical connection remaining between the layers 14 and 16. After a few days, the inflammation in the tissues will be reduced and new adhesions will not be forming. Any adhesions formed between the tissues and the layers will not have penetrated the layers. The layers will then resorb and the opposing tissues will have a plane between them free of adhesions.

Alternatively, the bond may be formed by compression of the two layers of the construct. In addition to compression, the application of heat, cold, texture or additional materials to one or more of the surfaces may be used. A material may be placed and compressed between the layers. Such material may increase or decrease the adhesion of the two layers to each other. The material may expand, contract or remain the same in the presence of water or other bodily fluids or substances. For example, hylauronic acid, hydrogel or other substances may be used between the layers.

Another method of forming a bond or physical approximation of the two layers is to configure the layers so they occupy one or more planes. For example, one layer may be folded over another at one or more edges. Such a configuration may be sufficient to provide temporary physical approximation of the layers.

Figure 8:
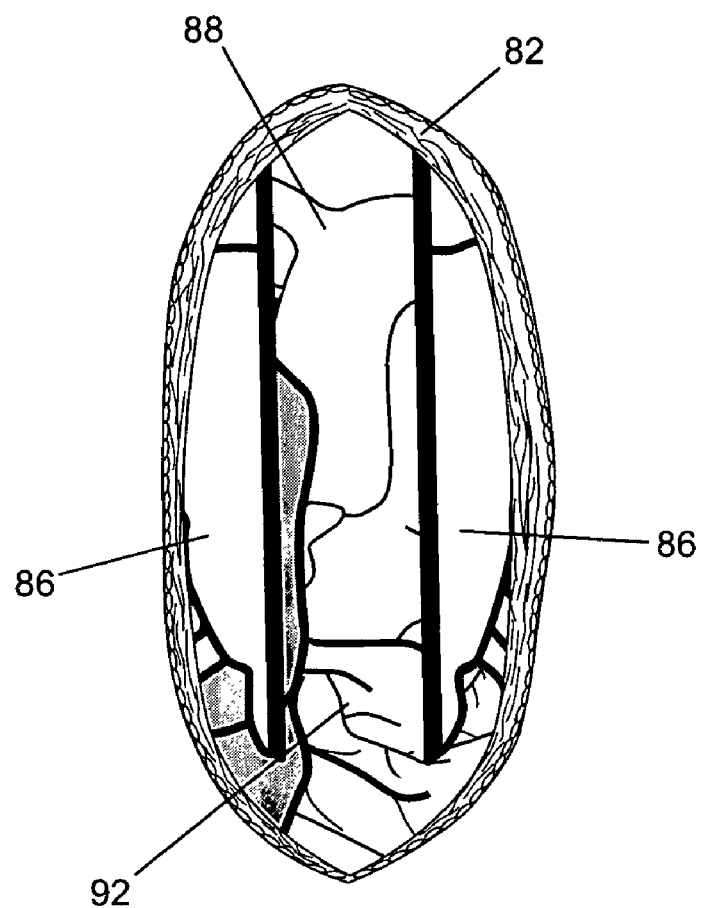
FIG. 8 is an illustration of the thorax of a living being after a median sternotomy has been performed.

One application of this construct is in the protection of thoracic structures during repeat median sternotomy. During thoracic surgery where a median sternotomy incision is used, the sternum is divided and the tissues posterior to the sternum are then accessible. FIG. 8 shows a median sternotomy incision where the sternum 86 is divided with a sternal saw and the underlying structures such as the aorta 88 and right ventricle 92 are exposed. Following the surgery within the thorax, the sternum is closed, commonly with steel wires and the subcutaneous and cutaneous tissues are then approximated. During the healing process the heart or great vessels may adhere to the posterior portion of the sternum or may be separated from the sternum by only a small distance. If subsequent surgery on the thorax requiring a median sternotomy is indicated and the heart or the aorta are adhered to the posterior portion of the sternum they may be damaged in the process of reopening the sternum with a sternal saw.

Figure 9:
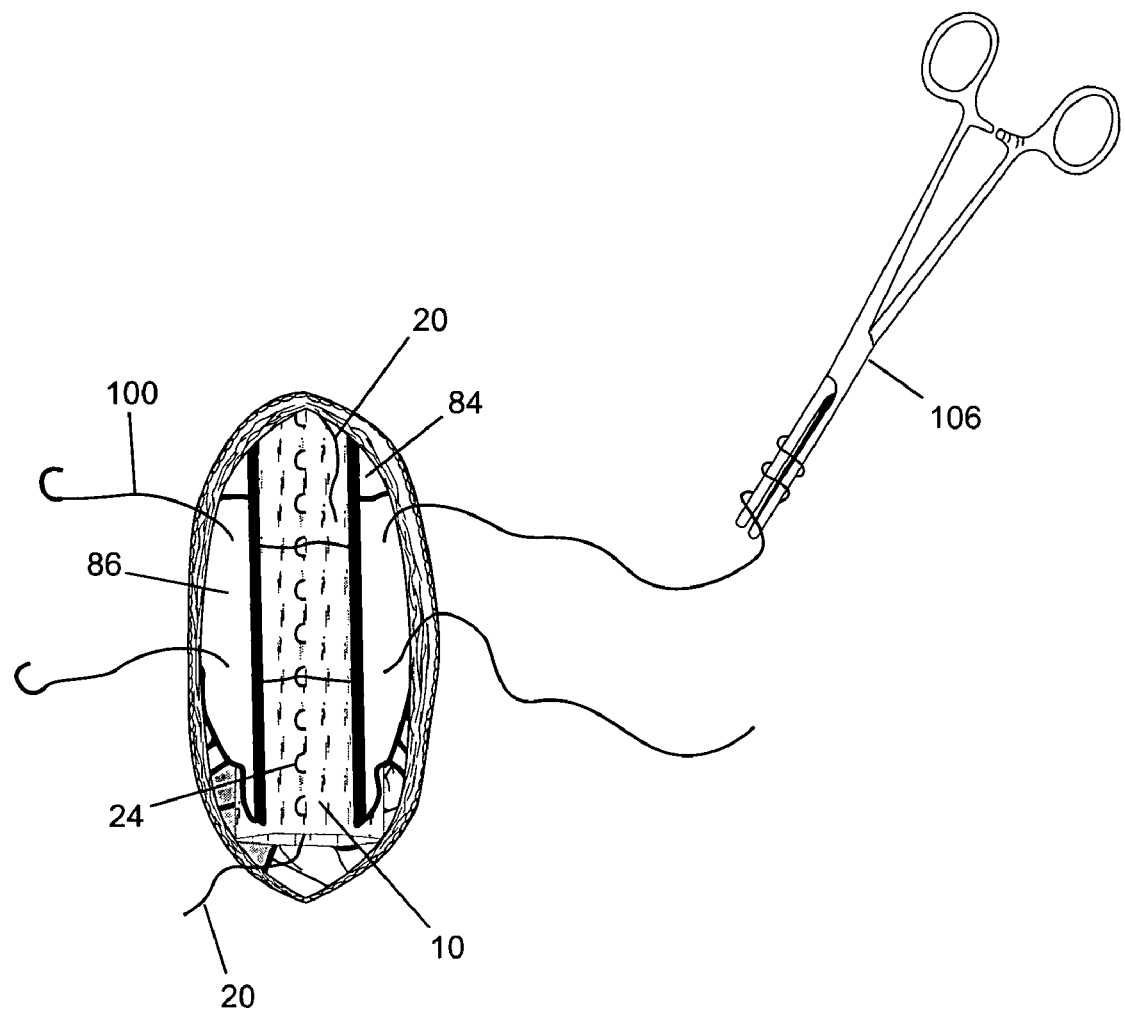
FIG. 9 is an illustration of the embodiment shown in FIG. 1 being placed posterior to the sternum as the sternum is being reapproximated.

As depicted in FIG. 9, the sternum 86 is divided and the construct 10 is placed posterior to the sternum 86, in order to protect the tissues posterior to the sternum. The sternum is reapproximated with sternal wires 100 which may be passed through the loops 24 of the construct 10. The locating limbs 20, if any, of the construct may be positioned so that they will be anterior to the sternum 86 when it is approximated. The construct 10 may extend superiorly beyond the superior portion of the sternum, the manubrium 84, and it may also extend inferiorly beyond the sternum. The extent of the construct beyond the sternum may be important in accessing the construct during subsequent reopening of the sternum. As the sternum 86 is approximated by applying tension on the sternal wires 100, optionally utilizing a tool 106, the wires 100 will pull the loops 24 and the construct 10 up against the posterior portion of the sternum 86. The approximation of the construct to the posterior portion of the sternum will promote healing and adhesion between the posterior sternum and the construct. The anterior layer of the construct will then be adjacent to the posterior portion of the sternum and the posterior layer of the construct will be adjacent the heart, great vessels and pericardium. In one embodiment, the construct may be made to promote adhesion of the anterior layer to the sternum (e.g., a porous polyurethane layer with collagen and b-FGF incorporated within the pores) and the posterior layer of the construct will be made to prevent adhesion to the heart and great vessels (e.g., a porous polyurethane layer with hylauronic acid, heparin and sirolimus incorporated within the pores). Another embodiment may render the anterior and posterior layers of the construct adherent to their respective adjacent tissue. Alternatively, the embodiment may prevent adherence to local tissues.

Figure 10:
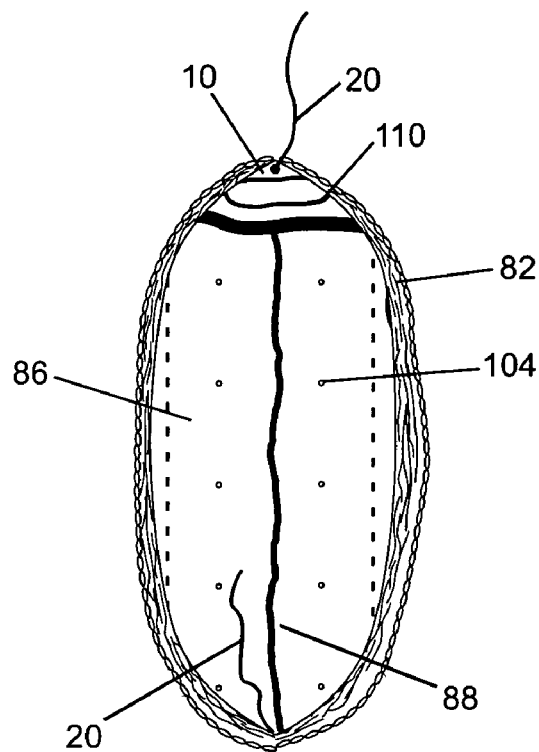
FIG. 10 is an illustration of the thorax of a living being before a subsequent sternotomy after construct as shown in FIG. 1 was placed following the initial sternotomy.
Figure 11A:
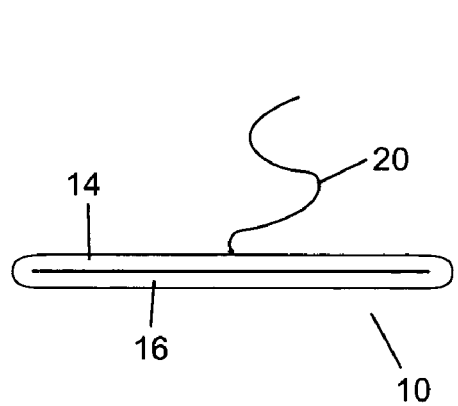
FIGS. 11 A and B are enlarged sectional views of a construct shown in FIG. 1, wherein a locating limb may be utilized for creating a space between layers of the construct.
Figure 11B:
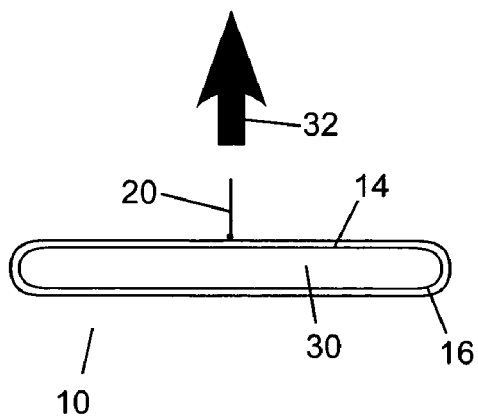

The sternum 86 and portions of the construct 10 upon a reoperation are shown in FIG. 10. In this figure, the skin and subcutaneous tissues 82 have been divided and the sternum 86 is exposed. The wires (100 of FIG. 9) which originally approximated the sternum 86 have been removed and only their residual holes 104 remain. Superior to the sternum 86, the superior edge of the anterior layer of the construct 10 is visible. The locating limb 20 is retracted to give exposure of the construct 10. FIG. 11A depicts a cross-section of the construct 10 with anterior 14 and posterior 16 layers and the locating limb 20 attached to the anterior layer 14. In FIG. 11B, tension (indicated by solid arrow 32) may be applied, e.g., in an anterior direction, to the locating limb 20 which is attached to the anterior layer 14 of the construct 10 causing the anterior layer 14 to pull away from the posterior layer 16 slightly, creating a small space 30 between the anterior and posterior layers. Referring again to FIG. 10, with this small space 30 between the anterior and posterior layers created by anterior tension on the locating limb 20, an incision 110 in the anterior layer of the construct 10 can be made without incising the posterior layer. In this manner, access is gained to the space between the anterior and posterior layers of the construct.

Figure 12:
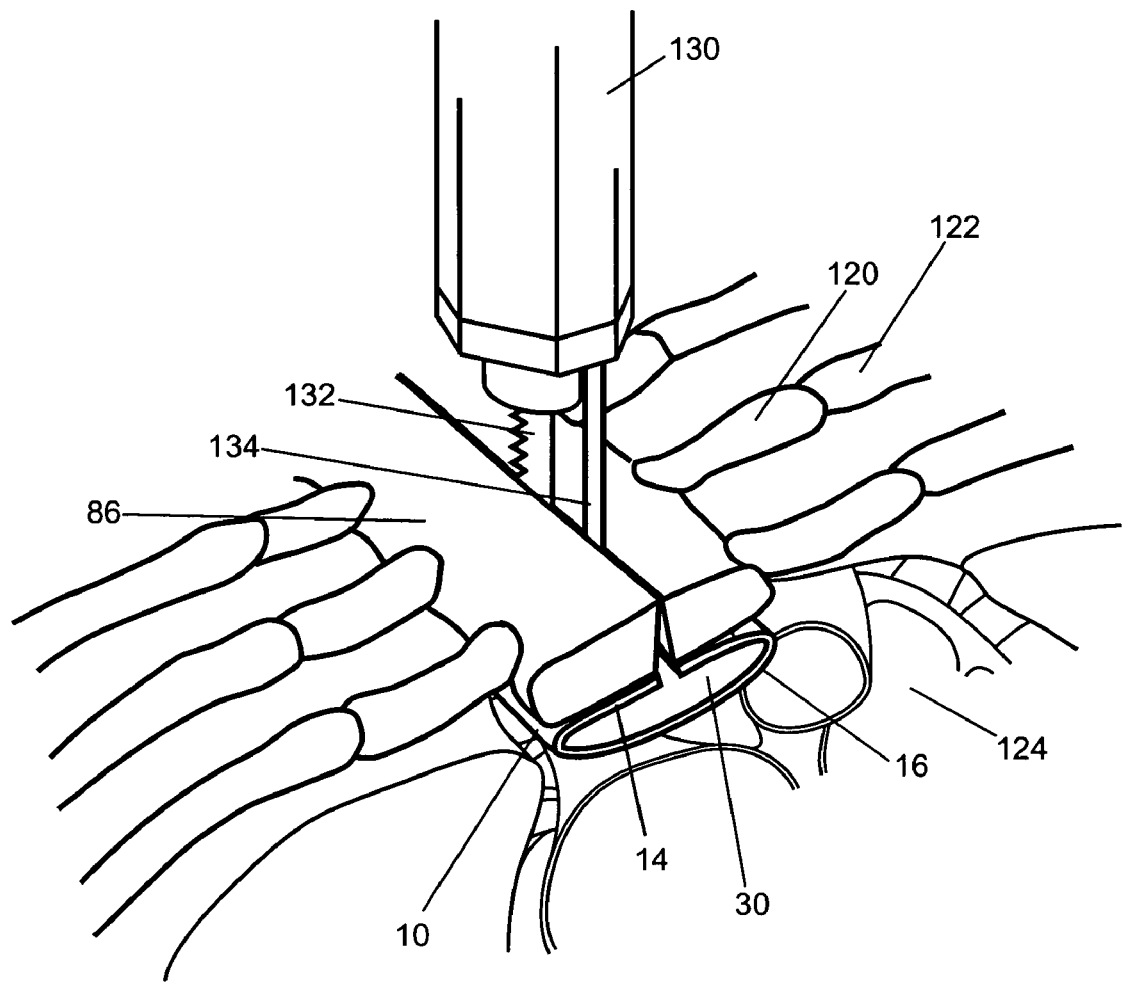
FIG. 12 is an isometric view in partial section of the construct posterior to the sternum where the saw is dividing the sternum and one or more layers of the construct while leaving one or more layers of the construct intact to protect the adjacent tissue from the saw.

FIG. 12 demonstrates the utility of the space 30 created between the anterior 14 and posterior 16 layers of the construct 10. In this figure, a sternal saw 130 with blade 132 and guide 134 is used to divide the sternum 86. To do so, the distal edge of the sternal blade 132 and guide 134 is inserted into the incision 110 in FIG. 10. The sternal saw blade 132 and guide 134 can now pass though the sternum 86 with their distal ends in the space 30 between the anterior 14 and posterior 16 layers of the construct 10. In this way, the tissues 124 posterior to the posterior layer 16 of the construct 10 are protected from the blade and guide of the sternal saw. Light retraction on the sternal saw 130 will maintain adequate space 30 to prevent the sternal saw from dividing the posterior layer of the construct. As disclosed above, there may be a protective layer incorporated into or in addition to the posterior layer of the construct to prevent the saw from dividing the posterior layer of the construct.

The construct may be shaped in a particular fashion prior to implantation. FIG. 13 is a cross-sectional view of the construct 140. The construct 140 has a particular non-planar shape with attachment loops 144 similar to those previously described. If the construct 140 is placed beneath the sternum or other tissue the curved nature of the construct will create a space between the middle of the construct and the tissue. FIG. 14 is a cross-sectional view of a construct 140 with attachment loops 144 positioned posterior to the sternum 86 with healed scar 88 from prior sternotomy. The construct is approximated to the sternum with sternal wires 100 and/or with an adhesive 150. The construct may extend beyond the edges of the sternum and approximated over the area of a harvested internal mammary artery. The construct 140 is non-planar and therefore a space is present between the construct and the sternum.

Figure 17:
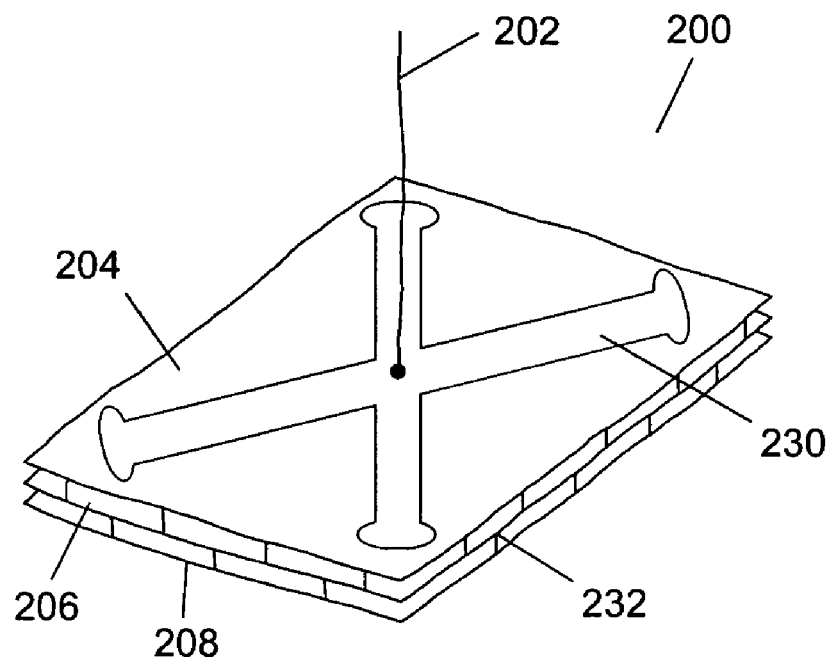
FIG. 17 is an isometric view of an embodiment of a device where the construct has structural supports.
Figure 18:
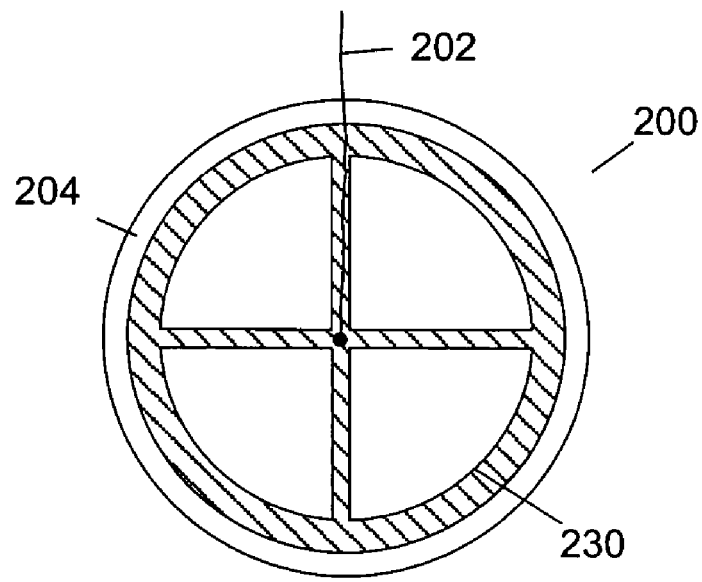
FIG. 18 is a top view of an embodiment of a device where the construct has structural supports.

Another embodiment of the construct may be used to prevent adhesions after procedures done through small incisions. For this application, the device may have additional features not described above. Specifically this embodiment of the device may be used for laproscopic surgery of any type or for procedures requiring a small incision. Furthermore, it may be used in the repair of non-iatrogenic wounds such as those caused by penetrating trauma (i.e. gunshot wounds, knife wounds, etc.). These iatrogenic or traumatic wounds may form adhesions to underlying structures. For example, laproscopic abdominal incisions may adhere to underlying bowel, uterus, fallopian tubes or other organs. The device shown in FIG. 15 is a multi-layered construct 200 with anterior layer 204 and posterior layer 206, similar to the construct described in FIG. 6. This embodiment contains a positioning member 202. The positioning member 202 may be used to position the construct 200 properly in relation to the incision or wound. Additionally the positioning member may be used to secure the construct in place. There may be more than one positioning member on the construct and the locating member may originate from either side or the edges of the construct or from within the construct. FIG. 16 demonstrates one embodiment of a construct 200, wherein at least a portion 215 of the construct 200 assumes or is arranged in a different plane than the remainder 220 of the construct 200. This may be utilized to ensure a desired shape of the construct after placement, such as a flat construct when placed against a flat surface with tension on the externally located positioning member 202. The construct may benefit from the incorporation of at least one additional mechanical support 230 within or attached to the construct 200 as shown in FIG. 17. The mechanical support 230 may be formed of any suitable material, such as those listed in Table 1. The at least one support 230 may be formed of the same or different material than the construct 200. The mechanical support 230 may have other properties, such as a source of biologically active agent or drug delivery, radiation delivery, or the support may perform some other function which has a biological or cellular impact. The construct 200 may have multiple layers 204, 206, 208 as previously discussed and the layers may have connections 232 between the layers that have mechanical, biological, imaging, therapeutic or other functions. The mechanical support(s) 230 may be provided in a desired shape to suit a specific need, such as the ring shape provided as shown in FIG. 18. The construct 200 or the mechanical support 230 may have a design which matches its desired clinical result. Furthermore, the positioning member 202 may be attached to the support 230 or may be attached to the construct independently.

Figure 19:
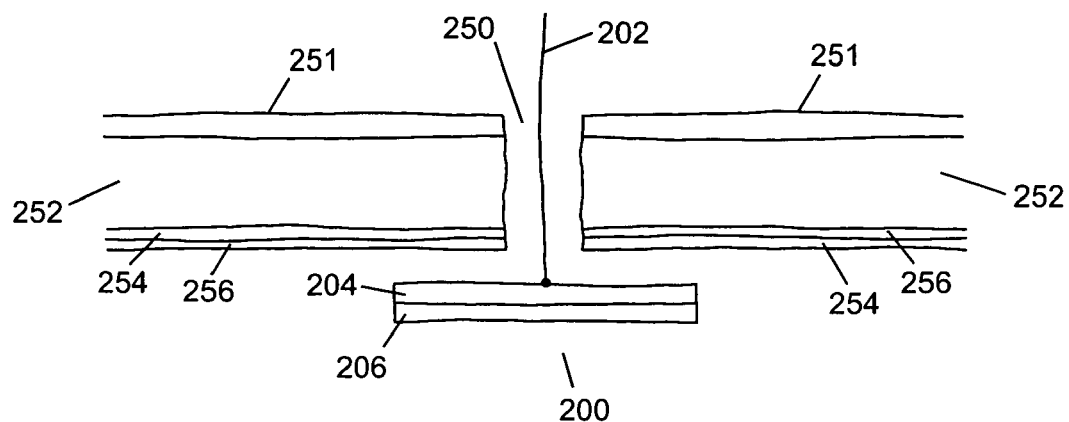
FIG. 19 is a cross-sectional view of a construct being placed in the abdomen of a patient.
Figure 20:
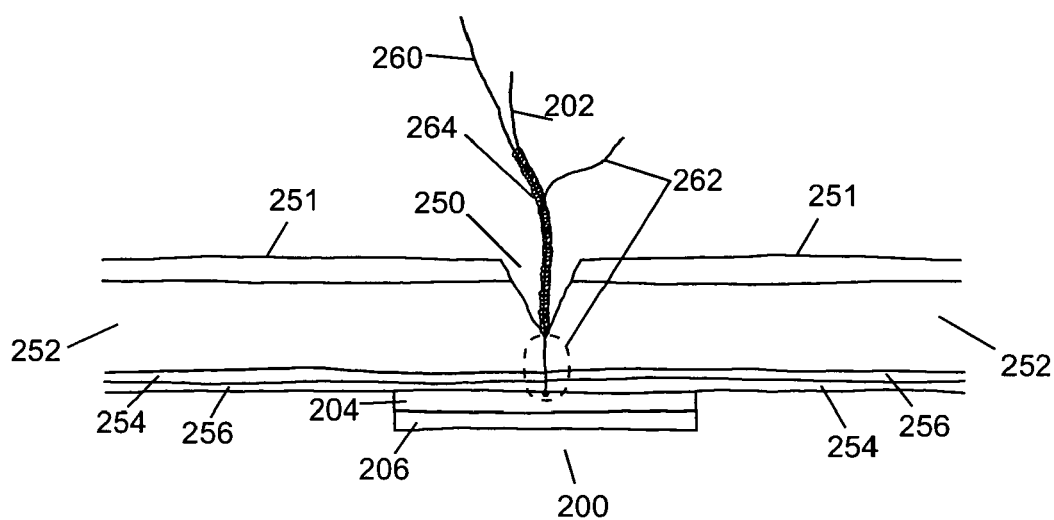
FIG. 20 is another cross-sectional view of a construct being placed in the abdomen of a patient.

One possible clinical use for the construct with a positioning member is in laproscopic surgery as previously discussed. FIGS. 19 and 20 demonstrate the utility of the construct 200 in being placed to prevent adhesions in the area of an incision (or wound) 250. The incision 250 is shown in the abdominal wall but may represent an incision in any tissue where adhesion prevention is desired. The incision 250 transects the cuticular and subcuticular layers 251, the subcutaneous tissue 252, the fascia 254 and the peritoneum 256. The construct 200 is placed in the desired plane in which adhesions across that plane are to be prevented. In the embodiment as shown depicted in FIG. 19, adhesions between the bowel (not shown) and the peritoneum 256 will be prevented. In FIG. 20, the incorporation of the construct 200 in the closure of the incision 250 is demonstrated. The fascia 254 and possibly the peritoneum 256 and a portion of the subcutaneous tissue 252 are approximated with a suture which has opposing sides 260 and 262 which are tied together to form a knot 264. This suture closes the defect in the abdominal wall and the construct 200 is placed just inferior to the fascia 254 and peritoneum 256. As depicted here, the construct covers the incision and forms a mechanical barrier between the incision and underlying tissues. The construct 200 may be held in place by incorporating the positioning member 202 within a knot with the suture. After the suture knot 264 is tied, a remaining portion of the suture 260 or 262 may be tied to the positioning member 202, as this would serve to firmly secure the construct 200 in place.

Delivery of the present invention as an anti-adhesion construct into a small incision or into the abdominal or thoracic cavity through a small incision may be accomplished in a number of ways. It may be possible to simply push the construct into the incision with a finger. Alternatively, a device or tool may be utilized to aid accurate and reliable delivery of the anti-adhesion construct. Shown in FIG. 21 is a delivery system 300 with shaft 301 and cap 302 to deliver a construct 200 into an incision through a trocar (not shown). The delivery system 300 and construct 200 are placed within a trocar adapter tube 320 with stop 322. The trocar adapter tube 320 is placed into the top of the trocar until the stop 322 is reached. This will pass the valve (not shown) and be positioned so the construct 200 can be easily advanced down the trocar and into a cavity using the delivery system 300.

FIG. 22 shows the delivery system 300 being used to advance the construct 200 through an incision 250 without a trocar. The construct 200 may be rolled as shown in FIG. 21, flexed as shown in FIG. 22, or otherwise manipulated to fit into or through the incision 250.

Figure 23:
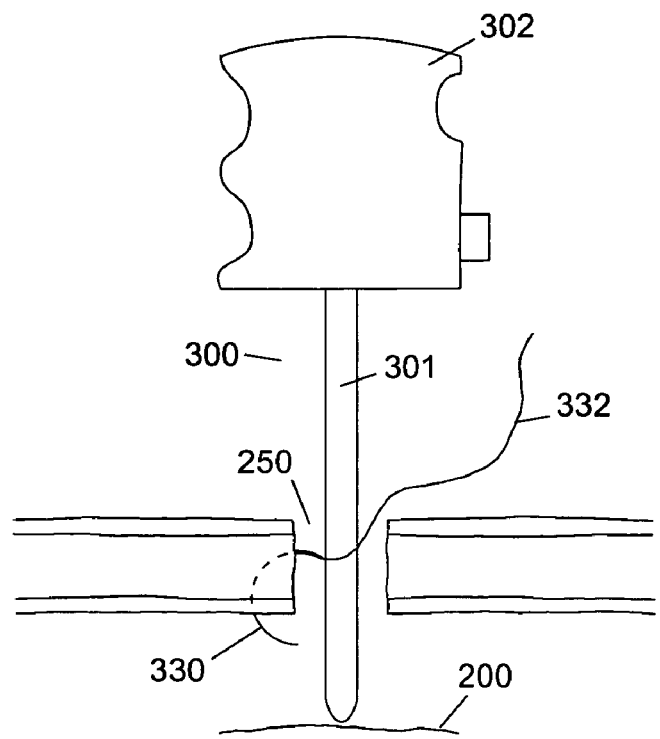
FIG. 23 is cross-sectional view of a delivery system placing the construct in a body cavity and positioning it so the fascia may be suture together.

FIG. 23 demonstrates the utility of having a delivery system 300 to manipulate the construct 200 within an incision 250. The delivery system 300 can position the construct so the incision can be closed with a needle 330 and suture 332. The delivery system holds the construct near or adjacent to its end by retaining the positioning member of the construct within its cap 302 and running through the interior of the length of shaft 301.

Figure 24:
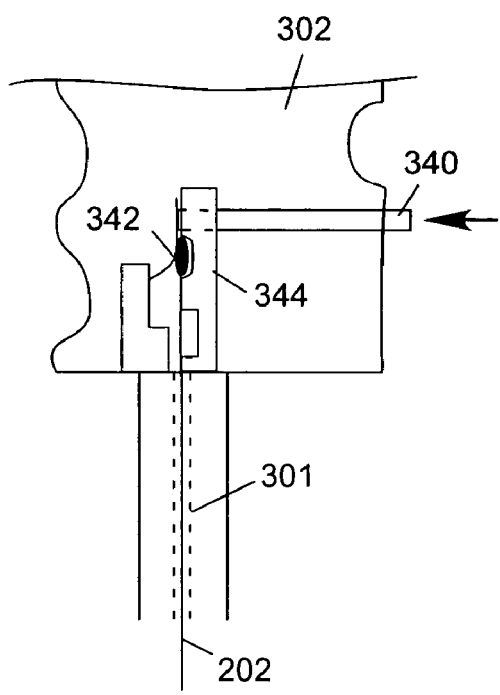
FIG. 24 is a cross-sectional view of the interior of a delivery system for retaining the positioning member of the construct.
Figure 25:
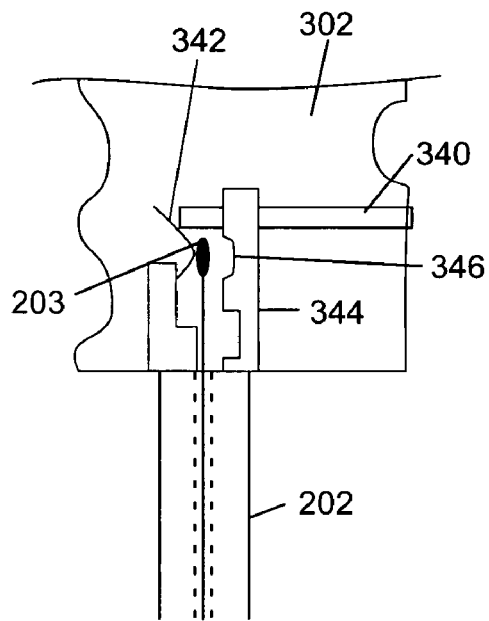
FIG. 25 is a cross-sectional view of the interior of a delivery system releasing the positioning member of the construct.

FIGS. 24 and 25 demonstrate one means of releasably retaining the positioning member 202 within the cap 302 of the delivery system. In FIG. 24, the positioning member 202 extends into the cap 302 through a hollow shaft 301. Within the cap 302, there is a stationary member 344 and a spring 342. The positioning member is held between the spring 342 and the stationary member 344. As can be seen in FIG. 25, a pin or button 340 is advanced into the spring 342 which moves it away from the stationary member 344 and releases the positioning member 202. The positioning member 202 may have an enlargement 203 at or near its proximal end which fits into a recess 346 in the spring and/or the stationary member 344. This recess may allow the delivery system to hold the positioning member against significant force until it is released by voluntarily moving the spring. There are many ways to releasably retain the positioning member. Other methods may include cutting the positioning member, having the positioning member snap apart or otherwise separate. The delivery system enables the user to position the construct through an incision and release it at the desired time.

An additional use for this technology would be providing an anti-adhesion barrier to any material which may be implanted either temporarily or permanently in or upon the body of a living being. For example, metal plates are often used in orthopedic or neurosurgery operations and the surface of the plate is in direct contact with tissue. This interface can damage adjacent tissue. One specific example is plates on the anterior body of cervical vertebrae can erode into the posterior wall of the esophagus. In addition to providing anti-adhesion and protection of surrounding tissues, covering implantable materials also provides a plane for future dissection, would another operation be necessary. This may be very beneficial in spine surgery and other surgeries where adhesions greatly influence the ease of any subsequent operations and may lead to inadvertent injury of adjacent tissue during their dissection. This technology could also be used with artificial organs and transplant organs to prevent unwanted adhesions to these structures. Artificially engineered organs and other tissues (bone, cartilage, etc.) may not have a well defined organ capsule as natural organs do and this technology may be used create an adhesion free cavity for the organ and would define a surgical plane should reoperation be necessary.

It should be understood that the foregoing disclosure and description of the present invention are illustrative and explanatory thereof and various changes in the size, shape, and material composition, as well as in the description of the preferred embodiment, may be made without departing from the spirit of the invention.

What is claimed is:

1. An implantable device for the prevention of adhesions comprising a plurality of layers, wherein said plurality of layers comprises at least an anterior and posterior layer, said anterior and posterior layers each having an outer and inner surface, said outer surfaces serving to promote adhesion to tissue and said inner surfaces serving to resist adhesion to tissue, said plurality of layers having at least one releasable attachment means arranged between said layers, said releasable attachment means being arranged to attach said layers together, wherein after implantation, said releasable attachment releases, whereupon said plurality of layers are completely releasably separate.

2. The device of claim 1 wherein at least a portion of at least one of said layers comprises a plurality of pores.

3. The device of claim 2 further comprising at least one additive component.

4. The device of claim 3 wherein said additive component comprises at least one member selected from the group consisting of biologically active agent, carrier material, fibrous materials, particulate materials, and plasticizers.

5. The device of claim 3 wherein said additive component is contained within said plurality of pores.

6. The device of claim 3, wherein said additive component is located in at least one of said pores and said at least one layer.

7. The device of claim 3, wherein said additive component comprises at least one of an adhesion promoter material and an adhesion retarding material.

8. The device of claim 3, wherein said additive component comprises at least one structural agent.

9. The device of claim 1 wherein the inner surfaces of said anterior and posterior layers are substantially non-porous.

10. The device of claim 9 wherein the outer surfaces of said anterior and posterior layers are porous.

11. The device of claim 9 wherein said substantially non-porous layers are impermeable to fluid.

12. The device of claim 1 further comprising at least one additive component.

13. The device of claim 12 wherein said additive component comprises at least one member selected from the group consisting of biologically active agent, carrier material, fibrous material, particulate material, and plasticizer.

14. The device of claim 12 wherein said additive component comprises a biologically active agent, said biologically active agent being arranged to be delivered by the device through a period of finite duration.

15. The device of claim 14 wherein said biologically active agent is released at a controlled rate.

16. The device of claim 12, wherein the additive component affects the formation of adhesion between tissue and said device.

17. The device of claim 1 further comprising at least one intervening layer of material between said anterior and posterior layers, said intervening layer being arranged to reduce adhesion or friction between said anterior and posterior layers.

18. The device of claim 1, wherein said releasable attachment means comprises at least one member selected from the group consisting of sutures, staples, clips, magnets, static bonds, physically interlocking components, adhesives, salts, carbohydrates, gelatins, and hydrogels.

19. The device of claim 1, wherein said releasable attachment means is resorbable.

20. The device of claim 19, wherein said plurality of layers are resorbable.

21. The device of claim 20 wherein said releasable attachment means is resorbed faster than said layers.

22. The device of claim 1 wherein said layers are attached by said releasable attachment means through at least one point.

23. The device of claim 1 wherein said layers are attached by said releasable attachment means along at least one edge.

24. The device of claim 1 further comprising a locating means.

25. The device of claim 24, wherein said locating means comprises at least one locating limb.

26. The device of claim 25, wherein said locating limb may be attached to at least one of said outer surface and said inner surface.

27. The device of claim 25, wherein a single locating limb is attached to at least one of said outer surface and said inner surface at multiple locations.

28. The device of claim 1 further comprising securing means being arranged to secure said device to tissue.

29. The device of claim 28 wherein, securing means comprises at least one loop arranged on said outer surfaces of the device.

30. The device of claim 29 wherein said securing means comprises an adhesive applied to said device.

31. The device of claim 28, wherein said securing means comprises at least one of tabs, magnets and staples.

32. The device of claim 1, wherein at least one layer comprises a non-resorbable material.

33. The device of claim 1, wherein at least one layer comprises a resorbable polymer material.

34. The device of claim 1, arranged to promote local adhesions of at least two tissues to one another.

35. The device of claim 1, further comprising at least one reinforcing material.

36. The device of claim 35, wherein said reinforcing material is arranged as a layer.

37. An implantable device for the prevention of adhesions comprising a plurality of layers, wherein said plurality of layers comprises at least an anterior layer and a posterior layer, said anterior and posterior layers each having an outer and inner surface, each of said anterior and posterior layers having a porosity comprising a plurality of pores, said porosity varying across the thickness of each of said anterior and posterior layers, and further wherein said varying porosity comprises a gradient, wherein said gradient comprises greater porosity towards said outer surface and reduced porosity towards said inner surface.

38. The device of claim 37, further comprising at least one additive component.

39. The device of claim 38 wherein said additive component comprises at least one member selected from the group consisting of biologically active agent, carrier material, fibrous material, particulate material, and plasticizer.

40. The device of claim 38, wherein said additive component is contained within said plurality of pores.

41. The device of claim 38, wherein said additive component comprises a biologically active agent, said biologically active agent being arranged to be delivered by the device through a period of finite duration.

42. The device of claim 41, wherein said biologically active agent is released at a controlled rate.

43. The device of claim 38, wherein said additive component affects the formation of adhesion between tissue and said device.

44. The device of claim 37 further comprising at least one intervening layer of material located between said layers, said intervening layer being arranged to reduce adhesion or friction between said layers.

45. The device of claim 37 further comprising a releasable attachment means, said releasable attachment means being arranged so as to attach said layers together.

46. The device of claim 45, wherein said releasable attachment means comprises at least one member selected from the group consisting of sutures, staples, clips, magnets, static bonds, physically interlocking components, adhesives, salts, carbohydrates, gelatins, and hydrogels.

47. The device of claim 45 wherein upon implantation, said releasable attachment means releases, whereupon said layers are releasably separated.

48. The device of claim 45 wherein said releasable attachment means is resorbable.

49. The device of claim 48, wherein said plurality of layers are resorbable.

50. The device of claim 49 wherein said releasable attachment means is resorbed faster than said layers.

51. The device of claim 45, wherein said layers are attached by said releasable attachment means at one or more points.

52. The device of claim 51, wherein said layers are attached along at least one edge.

53. The device of claim 52, wherein said layers are attached along all the edges thereby forming a substantially sealed space.

54. The device of claim 37 further comprising a locating means.

55. The device of claim 37 further comprising securing means arranged to secure said device to tissue.

56. The device of claim 55 wherein said securing means comprises at least one loop arranged on a surface of the device.

57. The device of claim 55 wherein said securing means comprises an adhesive applied to said device.

58. The device of claim 37, wherein said varying porosity comprises pores varying in at least one of size and number.

59. An implantable device for the prevention of adhesions comprising a plurality of layers, wherein said plurality of layers comprises at least an anterior layer and a posterior layer, said anterior and posterior layers each having an outer and inner surface, said outer surfaces serving to promote adhesion to tissue and said inner surfaces serving to resist adhesion to tissue, at least a portion of said inner surfaces opposing each other, said plurality of layers having at least one releasable attachment means arranged between said layers, said releasable attachment means being arranged to attach said layers together, wherein after implantation, said releasable attachment releases, whereupon said plurality of layers are no longer attached to one another.

* * * * *